United States Patent
Vishnevsky

[11] Patent Number: 5,868,691
[45] Date of Patent: Feb. 9, 1999

[54] POSTURE TRAINING DEVICE

[76] Inventor: John Vishnevsky, N59 W38465 Kohl La., Oconomowoc, Wis. 53066

[21] Appl. No.: 968,460

[22] Filed: Oct. 15, 1996

[51] Int. Cl.⁶ .............................. A61F 5/00; A61G 15/00
[52] U.S. Cl. ............................................. 602/19; 128/845
[58] Field of Search ................................. 602/19, 17, 18, 602/32, 36, 5; 128/874, 845, 846, 869, 870, DIG. 19; 2/44, 45

[56] References Cited

U.S. PATENT DOCUMENTS

| | | | |
|---|---|---|---|
| 1,581,791 | 4/1926 | Davison | 2/44 |
| 3,315,671 | 4/1967 | Creelman | 128/870 |
| 3,897,776 | 8/1975 | Gaylord, Jr. | 128/DIG. 19 X |
| 4,226,231 | 10/1980 | Anderson | 128/870 |
| 4,594,999 | 6/1986 | Nesbitt | 128/870 X |
| 5,086,757 | 2/1992 | Lestini | 602/19 X |
| 5,179,942 | 1/1993 | Drulias et al. | 602/19 X |
| 5,199,940 | 4/1993 | Morris et al. | 602/19 |
| 5,226,874 | 7/1993 | Heinz et al. | 602/19 |
| 5,435,563 | 7/1995 | Salvatore | 128/870 X |

Primary Examiner—Richard J. Apley
Assistant Examiner—Denise Pothier
Attorney, Agent, or Firm—Reinhart, Boerner, Van Deuren, Norris & Rieselbach, s.c.

[57] ABSTRACT

A posture training device comprising a substantially rigid support member including a plurality of slots and a plurality of straps. The straps are detachably coupled to the support member by inserting and sliding each of the straps into and through one of the slots. The slots extend between the support member's two opposing outer surfaces that are aligned substantially perpendicular to the individual's back when the device is worn. Each strap includes couplers at the ends of the strap for connecting ends each strap.

19 Claims, 3 Drawing Sheets

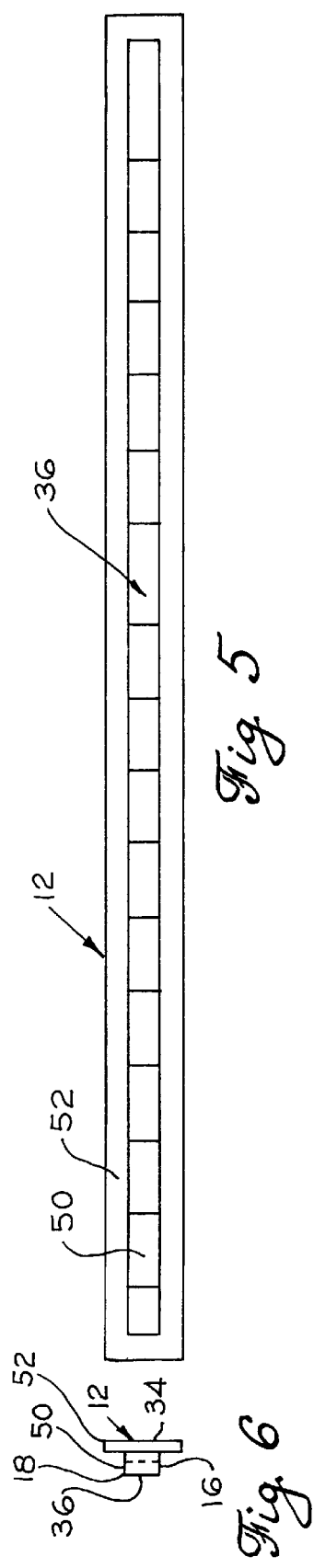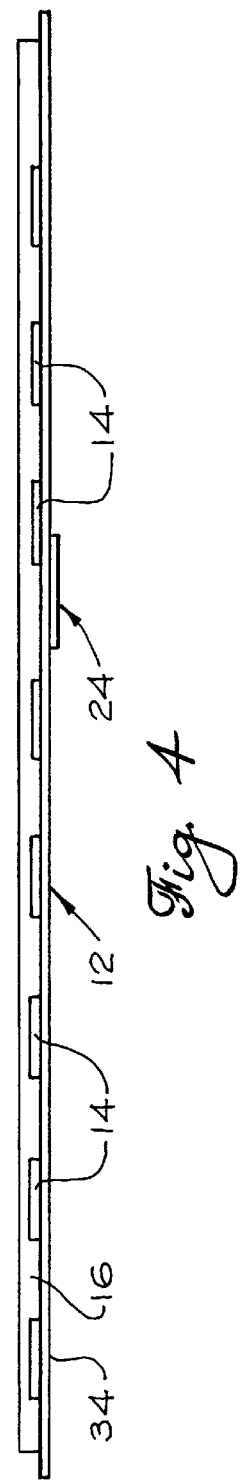

POSTURE TRAINING DEVICE

BACKGROUND OF THE INVENTION

The present invention generally relates to a posture training device. More particularly, the present invention relates to a device to improve a person's posture and train the person's back muscles to maintain the improved posture.

Some individuals have poor posture which has adverse effects. For example, poor posture is generally unattractive. Many people perceive individuals with upright posture as interested and alert, while individuals who slouch or stoop are viewed as lazy or awkward. These perceptions influence whether others positively view a person's work, or these perceptions can negatively affect how others regard the person's social status. In addition to being socially undesirable, poor posture causes various health problems. Among these health problems are curvature of the spine and a chronic stooping condition.

Health problems arise in part because poor posture is habitual and difficult to correct. Correction techniques which use verbal reminders can be ineffective. Reminders may fail because most people do not consciously choose their posture. Rather, posture is a position that the body's muscles are trained to assume.

To train the body's back muscles, devices are effective. One device is a restraint which physically forces the back's muscles to maintain the body in an upright position. When a person repeatedly wears the restraint, the muscles revert to proper posture position even at times when the restraint is not worn.

Thus, people need devices that correct posture and train muscles to maintain proper posture. Ideally, these devices are comfortable, portable and easily fastened and removed.

It is therefore an object of the invention to provide a novel posture training device and method to effectively train a person to maintain substantially upright posture.

It is another object of the invention to provide an improved posture training device that is comfortable to wear.

It is a further object of the invention to provide an improved posture training device that easily attaches to a person's body and is easily removable as well.

It is yet another object of the invention to provide an improved posture training device that is portable.

Other objects, features and advantages of the present invention will be apparent from the following description of the preferred embodiments thereof, taken in conjunction with the accompanying drawings described below wherein like components have like numerals throughout the several views.

BRIEF DESCRIPTION OF THE DRAWINGS

FIG. 4 is a side view of the posture training device shown in FIG. 3.

FIG. 5 is a back view of the posture training device shown in FIGS. 3 and 4.

FIG. 6 is a top view of the posture training device shown in FIGS. 3–5.

DETAILED DESCRIPTION OF PREFERRED EMBODIMENTS

Figures 1, 2:
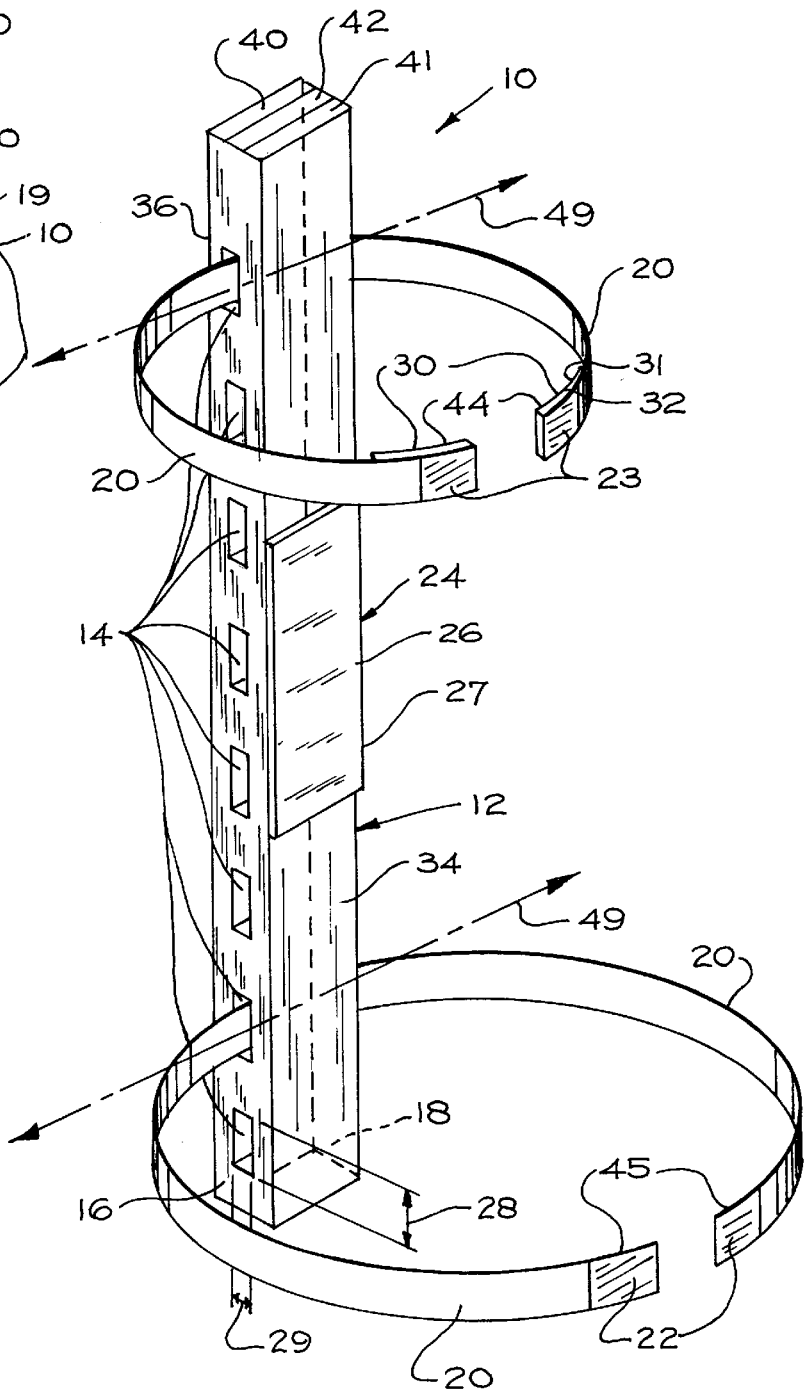
FIG. 1 is an isometric view of a posture training device constructed in accordance with one preferred embodiment of the invention.
FIG. 2 is a side view of a person wearing the posture training device shown in FIG. 1.
Figure 3:
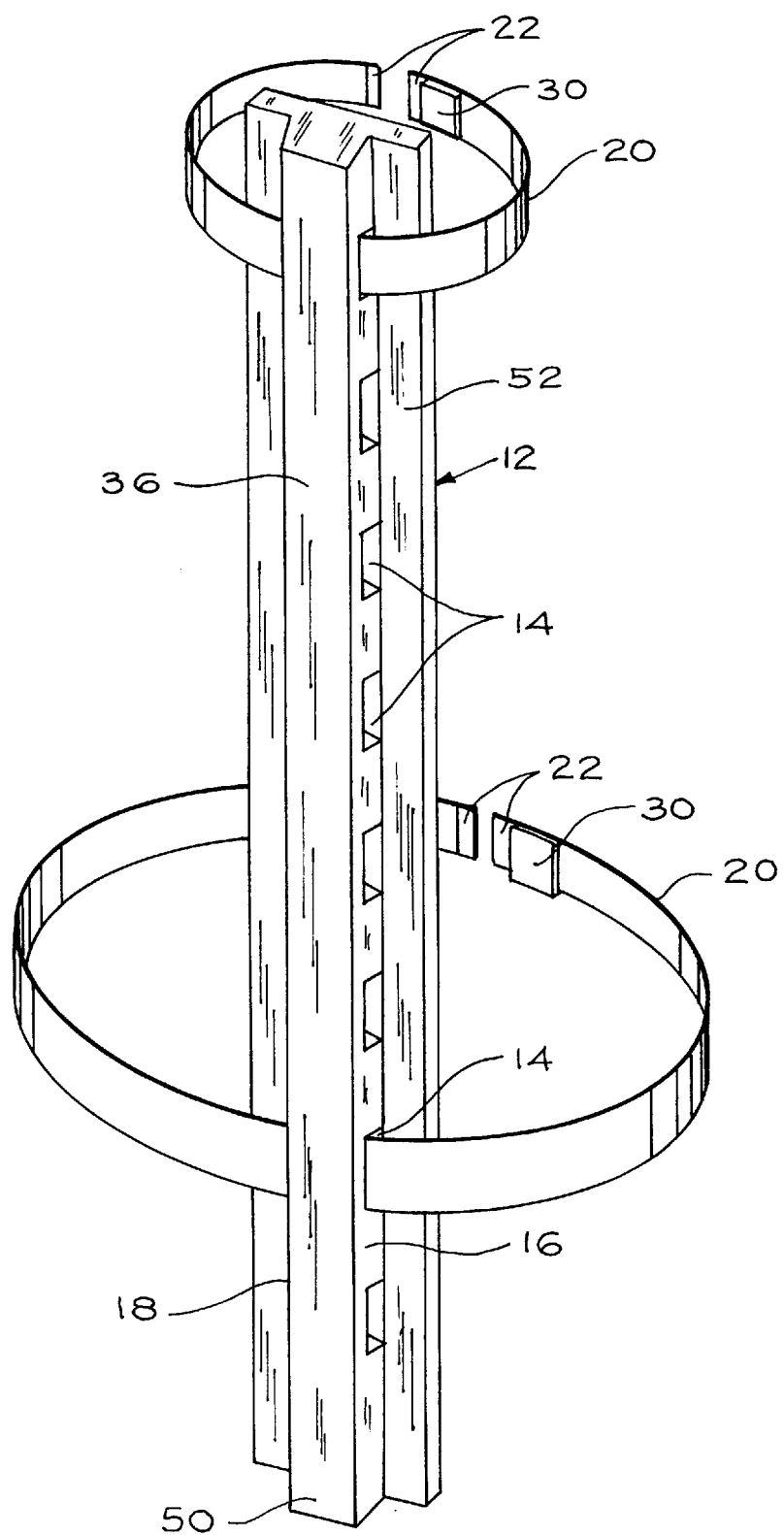
FIG. 3 is an isometric view of a posture training device constructed in accordance with an alternative embodiment of the invention.

Referring to the Figures and more particularly to FIG. 1, a posture training device constructed in accordance with one preferred embodiment of the invention is illustrated at 10. The posture training device 10 preferably includes a substantially rigid support member 12 with a plurality of slots 14, a pad 24, a plurality of straps 20 with couplers 22, 23 at the ends 44, 45 of each strap 20 and cushions 30 at one end 44 of each strap 20.

The rigid support member 12 preferably includes at least one substantially flat surface. The support member 12 can comprise various substantially non-deformable, non-malleable objects, such as a wooden board or a sheet of hard plastic. In one preferred embodiment, outer surfaces 16, 18, 34, 36 of the support member 12 have a smooth finish and substantially dull or rounded edges and corners to enable a user to comfortably handle the device 10. Opposing outer surfaces 16 and 18 are preferably substantially parallel along an axis substantially perpendicular to a user's back 19.

The support member 12 preferably includes a pad 24 attached to its front surface 34 for additional user comfort. The pad 24 can be attached to the front surface 34 by various methods including stapling, tacking, nailing or gluing the pad 24 to the front surface 34. Preferably, the attachment method leaves only small gaps between the deformable surface 26 and the front surface 34. Moreover, the attachment method does not expose sharp or jagged edges to give the user safety and comfort. The pad 24 extends across the front surface 34 for a sufficient length to provide contact between the pad 24 and a user's back 19.

The pad 24 preferably comprises a deformable surface 26 and compressible stuffing 27. The material for the deformable surface 26 should be substantially puncture resistant and resilient. A variety of materials can be used, including cloth, plastic, rubber and leather. The pad 24 is formed by stretching the deformable surface 26 substantially taut over the compressible stuffing 27 and attaching the deformable surface 26 to the front surface 34. The deformable surface 26 and the pad 24 preferably completely envelopes the compressible stuffing 27.

The compressible stuffing 27 can comprise a variety of deformable resilient materials. In one preferred embodiment, the compressible stuffing 27 comprises a single piece of foam rubber or another material well known in the art. The single piece of compressible stuffing 27 should be large enough to prevent it from moving through any gaps between the deformable surface 24 and the front surface 34.

In addition to the pad 24, the support member 12 includes a plurality of slots 14 that extend substantially perpendicular to and between the two opposing outer surfaces 16, 18 which are aligned substantially perpendicular with the user's back 19. The slots 14 extend along the width of the front surface 34 and back surface 36 and have openings in each of the opposing outer surfaces 16, 18. This slot 14 location enables the straps 20 to extend away from the support member 12 substantially parallel to the plane (not shown) formed by the user's back 19, typically preventing the user's back 19 from contacting the slots 14 or the straps 20.

As shown in FIG. 1, the slots 14 can have a substantially rectangular cross sectional shape with a slightly larger size than the straps 20. The rectangular cross sectional shape of the slots 14 preferably has a greater height 28 than width 29. In one preferred embodiment, the cross section of the slots 14 has an aspect ratio height 28 to width 29 of approximately five to one. With slots 14 of this shape and approximate aspect ratio, the straps 20 slide through the slots 14 without substantial resistance. The slots 14 preferably include rounded edges at and near the outer surfaces 16, 18 to facilitate such sliding.

Preferably, many slots 14 are provided in the support member 12 that is relatively long, while maintaining the light weight, ease of handling and portability of the support member 12.

The slots 14 can be formed by various methods. In one preferred embodiment, the slots 14 are created by machining or sawing rectangles in the support member 12. In an alternative embodiment, the slots 14 are created by the assembly of multiple sheets 40, 41, 42 of the support member 12. The support member 12 comprises a front sheet 41, a back sheet 40 and multiple interstitial sheets 42. In this embodiment, one face of the front sheet 41 comprises the front surface 34, and one face of the back sheet 40 comprises the back surface 36 of the support member 12. The interstitial sheets 42 are coupled to the front sheet 41 and back sheet 40. The interstitial sheets 42 are spaced in such a manner that spaces between the interstitial sheets 42 comprise the slots 14.

The slots 14 define an axis 49 for the straps 20 to slide along and through and the straps 20 are detachably coupled to the support member 12. In one preferred embodiment, the device 10 includes a pair of straps 20 for attachment to a user's head and waist, as shown in FIG. 2. Alternatively, straps 20 can be provided to attach the device 10 to different body parts.

The straps 20 preferably comprise a distensible, thin strip of material, which can comprise a variety of materials. One preferred material is rubber, however, other materials with elastic properties can be used. The straps 20 preferably stretch more easily along their length than along their width. For the user's comfort, the straps 20 should have a non-abrasive, relatively smooth finish.

Further, the location of the slots 14 enable the user to comfortably adjust and wear the straps 20 such that the user's back 19 does not contact the slots 14 or the straps 20.

Preferably, the unstretched straps 20 have a length slightly shorter than the length required to hold a small user. This short unstretched length forces most users to stretch the straps 20 to engage the couplers 22, 23. This stretch keeps tension in the straps 20 so that the device 10 stays in a position that forces the user to maintain proper posture. However, the straps 20 must have a sufficient length to avoid excessive stretching.

The ends 45, 44 of the straps 20 connect together with couplers 22, 23 to hold the device 10 to a user. In one preferred embodiment, the couplers 22, 23 consist of a conventional hook and corresponding loop connection system to provide easy fastening and removal. In this embodiment, some couplers 22, 23 on one end 45, 44 of the straps 20 comprise the hook connections, while the other couplers 22, 23 on the other ends 44, 45 of the straps 20 comprise loop connections. The hook couplers 22, 23 are attached to one face of the straps 20, and the loop couplers 22, 23 are attached to the opposing face of the straps 20. Various attachment methods well known in the art can be used.

Further, the straps 20 can include cushions 30 for comfort. In one preferred embodiment, the cushions 30 attach to the face of the straps 20 opposite the face occupied by the hook couplers 22, 23. The cushions 30 include a cover 31 and padding 32. The cover 31 can comprise cloth, plastic, rubber, leather or other materials well known in the art. Likewise, various materials well known in the art can comprise the padding 32. The cushions 30 can attach to the straps 20 by sewing, gluing, tacking or other methods well known in the art. When the user connects the straps 20 and attaches the device 10 to his or her body, the cushions 30 provide comfort at the pressure points where the straps 20 contact the body.

Referring to FIGS. 1 and 2, a user wears the device 10 by inserting the straps 20 into and through a pair of the plurality of slots 14. Preferably, the user aligns the straps 20 so that approximately equal portions of the straps 20 extend from each side of the support member 12. In this configuration, the ends 44, 45 align substantially with the front of the user's body enabling an easy strap 20 connection. The user positions the front surface 34 of the support member 12 parallel with his or her back 19, as shown in FIG. 2. With the support member 12 maintaining the user's back 19 in a relatively straight posture, the user stretches the straps 20 and connects the couplers 22, 23 at the ends 45, 44 of the straps 20. The slots 14 allow the straps 20 to be slid such that the couplers 22, 23 are located in an unobtrusive location after coupling. Consequently, the device 10 draws tightly against the user's body. The user wears the device 10 for intermittent time intervals to train his or her muscles to maintain proper posture.

A posture training device 10 constructed in accordance with an alternative embodiment of the invention is shown in FIGS. 3–6. In this preferred embodiment, the device 10 is constructed and operates similar to the device 10 shown in FIGS. 1 and 2. Accordingly, only the differences between these preferred embodiments is discussed below, focusing primarily upon the support member 12. In this embodiment, the support member 12 is preferably substantially T-shaped with the leg 50 of the T including opposing outer surfaces 16 and 18 again oriented substantially parallel along an axis substantially perpendicular to a user's back 19. While a variety of shapes can also be used, a T shape dimensioning the width of the leg 50 substantially equal to one half of the width of a top 52 of the T and dimensioning the height of the leg 50 substantially equal to twice the height of the top 52 has been found to provide surprisingly good therapeutic results. These preferred dimensions allow ease of use and light weight while retaining the beneficial substantially rigid characteristics of the present invention. Preferably all outer surfaces of the support member 12 are rounded as shown in FIGS. 3–6. The other functions of the support member 12 and the structures which can be coupled to the support member 12 are exactly the same and described previously herein.

While preferred embodiments of the invention have been shown and described, it will be clear to those skilled in the art that various changes and modifications can be made without departing from the invention in its broader aspects as set forth in the claims provided hereinafter.

I claim:

1. A posture training device, comprising:
    a substantially rigid support member including a plurality of slots extending between two opposing outer surfaces of said support member, with both of said opposing outer surfaces positionable to be aligned substantially perpendicular to a user's back; and
    a plurality of straps detachably coupled to said support member, each of said straps being inserted through one of said plurality of slots to detachably couple said straps to said support member.

2. The posture training device as claimed in claim 1, wherein said straps slide within said plurality of slots substantially along an axis defined by said slots.

3. The posture training device as claimed in claim 1, wherein each of said straps is distensible and resilient.

4. The posture training device as claimed in claim 1, wherein said support member is substantially T-shaped.

5. The posture training device as claimed in claim 1, wherein both ends of said straps include a coupler.

6. The posture training device as claimed in claim 5, wherein said couplers comprise hook and loop connection systems.

7. The posture training device as claimed in claim 1, wherein said straps include a plurality of cushions.

8. The posture training device as claimed in claim 7, wherein each of said plurality of cushions includes a cloth surface.

9. The posture training device as claimed in claim 1, wherein said support member is non-malleable.

10. The posture training device as claimed in claim 9, wherein said support member comprises wood.

11. The posture training device as claimed in claim 1, further including a pad coupled to said support member.

12. The posture training device as claimed in claim 11, wherein said pad includes a deformable surface comprising foam rubber.

13. A posture training device, comprising:
   a single substantially rigid support member comprising a rectangular cross section and including a plurality of slots extending between two opposing outer surfaces of said support member, both of said opposing outer surfaces positionable to be aligned substantially perpendicular to a user's back; and
   a plurality of straps, each strap inserted through one of said plurality of slots to detachably couple said straps to said support member, each of said straps sliding within said plurality of slots along an axis substantially perpendicular to said opposing outer surfaces, and each of said straps including a coupler for coupling both ends of said strap together.

14. A posture training device as claimed in claim 13, further including a pad comprising foam rubber, coupled to said support member.

15. A posture training device as claimed in claim 13, wherein each of said straps comprises an elastic material.

16. A posture training device as claimed in claim 13, wherein said couplers comprise hook and loop connection systems.

17. A posture training device to train muscles to maintain an upper body in a completely upright stance, comprising:
   a single substantially rigid support member having a T-shaped cross section and including a plurality of slots having a rectangular cross section extending along a width of said support member between two opposing outer surfaces of said support member, with both of said opposing outer surfaces positionable to be aligned substantially perpendicular to a user's back;
   a plurality of distensible and resilient straps, with each strap inserted through one of said plurality of slots to detachably couple said straps to said support member, with each of said straps sliding within said plurality of slots substantially along an axis defined by said slots, including a hook and loop coupler for coupling both ends together, and including a cloth covered foam rubber cushion; and
   a pad comprising foam rubber coupled to said support member.

18. A posture training device to train muscles to maintain an upper body in a completely upright stance, comprising:
   a single substantially rigid support member having a T-shaped cross section and including a plurality of slots having a rectangular cross section extending along a width of said support member between two opposing outer surfaces positionable to be of said support member, with both of said opposing outer surfaces aligned substantially perpendicular to a user's back;
   a plurality of distensible and resilient straps, with each strap inserted through one of said plurality of slots to detachably couple said straps to said support member, with each of said straps sliding within said plurality of slots substantially along an axis defined by said slots, including a hook and loop coupler for coupling both ends together, and including a cloth covered foam rubber cushion; and
   a pad comprising foam rubber coupled to said support member.

19. A method of training muscles to maintain substantially upright posture comprising the steps of:
   providing a single substantially rigid support member including a plurality of slots extending between two opposing outer surfaces of said support member, with both of said opposing outer surfaces positionable to be aligned substantially perpendicular with a user's back, including a plurality of elastic straps inserted through one of said plurality of slots to detachably couple said support member, with each of said straps sliding within said plurality of slots substantially along an axis defined by said slots, and including a coupler for coupling both ends together, with a cloth covered foam rubber cushion at the ends of the straps; and
   attaching the device to the user's body by placing the support member along the person's back and fastening the couplers on the ends of the straps together.

* * * * *